United States Patent
Fujita

(10) Patent No.: US 11,147,512 B2
(45) Date of Patent: Oct. 19, 2021

(54) PULSE WAVE DETECTION DEVICE AND BIOMETRIC INFORMATION MEASUREMENT DEVICE

(71) Applicant: OMRON HEALTHCARE CO., LTD., Muko (JP)

(72) Inventor: Reiji Fujita, Muko (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 357 days.

(21) Appl. No.: 16/144,244

(22) Filed: Sep. 27, 2018

(65) Prior Publication Data

US 2019/0021668 A1 Jan. 24, 2019

Related U.S. Application Data

(63) Continuation of application No. PCT/JP2017/012453, filed on Mar. 27, 2017.

(30) Foreign Application Priority Data

Apr. 5, 2016 (JP) .............................. JP2016-075966

(51) Int. Cl.
- *A61B 5/00* (2006.01)
- *A61B 5/02* (2006.01)
- *A61B 5/024* (2006.01)

(52) U.S. Cl.
CPC ................ *A61B 5/684* (2013.01); *A61B 5/02* (2013.01); *A61B 5/02438* (2013.01);
(Continued)

(58) Field of Classification Search
CPC ........... A61B 5/684; A61B 5/681; A61B 5/02; A61B 5/02438; A61B 5/6824; A61B 5/6831; A61B 2562/164; A44C 5/0053
See application file for complete search history.

(56) References Cited

U.S. PATENT DOCUMENTS

| 6,238,083 B1 * | 5/2001 | Hirano | ..................... A44C 5/14 224/168 |
| 2002/0151775 A1 | 10/2002 | Kondo | |

(Continued)

FOREIGN PATENT DOCUMENTS

| JP | S51-041285 A | 4/1976 |
| JP | H05-329117 A | 12/1993 |

(Continued)

OTHER PUBLICATIONS

Feb. 5, 2020 Search Report issued in European Patent Application No. 17778997.1.

(Continued)

*Primary Examiner* — Eric F Winakur
*Assistant Examiner* — Abid A Mustansir
(74) *Attorney, Agent, or Firm* — Oliff PLC

(57) ABSTRACT

There is provided a pulse wave detector. A body portion includes a pulse wave detection sensor which detects a pulse wave from an artery in a wrist of a user. A strip-shaped band member secures the body portion to the wrist. In a secured state where the body portion is secured to the wrist with the band member, the body portion is placed in a position where a process of an ulna in the wrist or a process of a radius in the wrist is exposed. The band member includes a first region, and a second region which is higher in stretchability than the first region. In the secured state, the second region is at least in contact with the process of the ulna in the wrist or the process of the radius in the wrist.

8 Claims, 9 Drawing Sheets

(52) U.S. Cl.
CPC .......... *A61B 5/681* (2013.01); *A61B 5/6824* (2013.01); *A61B 5/6831* (2013.01); *A61B 2562/164* (2013.01)

(56) References Cited

U.S. PATENT DOCUMENTS

| | | |
|---|---|---|
| 2004/0193059 A1 | 9/2004 | Inoue et al. |
| 2015/0282713 A1 | 10/2015 | Fei |
| 2016/0255921 A1* | 9/2016 | Hamada ................ D03D 3/005 |

FOREIGN PATENT DOCUMENTS

| | | |
|---|---|---|
| JP | 2002-191567 A | 7/2002 |
| JP | 2008-168054 A | 7/2008 |
| JP | 2010-137110 A | 6/2010 |
| JP | 2010-220948 A | 10/2010 |
| JP | 2013-137110 A | 7/2013 |
| WO | 2015-157712 A2 | 10/2015 |

OTHER PUBLICATIONS

Mar. 10, 2020 Office Action issued in Japanese Patent Application No. 2016-075966.

Jun. 20, 2017 International Search Report issued in International Patent Application No. PCT/JP2017/012453.

Apr. 12, 2018 International Preliminary Report on Patentability issued in International Patent Application No. PCT/JP2017/012453.

* cited by examiner

CIRCUMFERENTIAL DIRECTION OF WRIST

CIRCUMFERENTIAL DIRECTION OF WRIST

CIRCUMFERENTIAL DIRECTION OF WRIST

PULSE WAVE DETECTION DEVICE AND BIOMETRIC INFORMATION MEASUREMENT DEVICE

CROSS-REFERENCE TO RELATED APPLICATIONS

The disclosure of Japanese Patent Application No. 2016-075966 filed on Apr. 5, 2016, including specification, drawings and claims is incorporated herein by reference in its entirety.

The disclosure of International Patent Application No. PCT/JP2017/012453 filed on Mar. 27, 2017, including specification, drawings and claims is incorporated herein by reference in its entirety.

TECHNICAL FIELD

The present disclosure relates to a pulse wave detector and a biometric information measurement device.

BACKGROUND

A biometric information measurement device is known that, in a state where a pressure sensor is directly contacted with a living body portion through which an artery such as the radial artery in the wrist passes, can measure biometric information such as the heart rate, the pulse rate, or the blood pressure by using information detected by the sensor (for example, see Patent Literatures 1 to 3).

Patent Literature 1 discloses a biometric information measurement device in which an opening for avoiding the ulna is disposed in a portion that is to be wound around the back side of the hand in a state where the device is attached to the wrist, whereby the state where the device is attached to the wrist is enabled to be stably maintained.

Patent Literature 2 discloses a biometric information measurement device in which a band that is to be wound around the wrist, and that is stretchable and contractible in the winding direction is provided with: a marking portion that stretches or contracts in connection with stretching or contraction of the band, and that indicates the band wound strength depending on the degree of stretching or contraction of the band; and a reference button functioning as a reference for determining whether the degree of stretching or contraction indicated by the marking portion corresponds to the optimum band wound strength or not.

According to the biometric information measurement device, when the attachment of the device is performed by using the marking portion and the reference button, the device can be attached at the optimum band wound strength irrespective of the diameter of the wrist of the user.

Patent Literature 3 discloses a biometric information measurement device in which both end portions of a band portion that is to be wound around the wrist are divided into three parts, and one and other ends of the divided band parts are enabled to be respectively secured.

Patent Literature 1: JP-A-2008-168054
Patent Literature 2: JP-A-05-329117
Patent Literature 3: JP-A-S51-041285

Each of the biometric information measurement devices disclosed in Patent Literatures 1 and 2 is to be attached to the wrist by fastening and securing a housing which accommodates the pressure sensor portion, to the wrist with the single band. In the wrist, the ulna has a protruding portion. In the biometric information measurement devices of Patent Literatures 1 and 2, there is a possibility that the ulna may interfere the fastening of the band to worsen the feeling and easiness of attachment of the device, or, after attachment, displacement of the position of the device may occur.

When a highly stretchable material is used in the band, the feeling and easiness of attachment of the device can be improved. In the case of a band having a high stretchability, after the device is secured to the wrist, however, there arises a possibility that displacement of the position of the pressure sensor portion may be caused by stretching or contraction of the band portion, and therefore it is difficult to accurately measure biometric information.

In the biometric information measurement device of Patent Literature 3, pressure sensors are secured to the divided parts, respectively, thereby enabling the pressing positions of the pressure sensors to be adjustable. However, the pressure sensors are disposed on the band itself, and therefore there is a high possibility that the positions of the pressure sensors may be displaced by a motion of the hand. As a result, the device cannot accurately measure biometric information.

Although biometric information measurement devices which detect a pressure pulse wave by using a pressure sensor have been described above, similar problems occur also in a biometric information measurement device in which, for example, a volume pulse wave is detected by using a photoelectric sensor.

SUMMARY

According to an aspect of the embodiments of the present disclosure, there is provided a pulse wave detector comprising: a body portion including a pulse wave detection sensor which detects a pulse wave from an artery in a wrist of a user; and a strip-shaped band member for securing the body portion to the wrist, wherein in a secured state where the body portion is secured to the wrist with the band member, the body portion is placed in a position where a process of an ulna in the wrist or a process of a radius in the wrist is exposed, wherein the band member includes a first region, and a second region which is higher in stretchability than the first region, and wherein in the secured state, the second region is at least in contact with the process of the ulna in the wrist or the process of the radius in the wrist.

According to an aspect of the embodiments of the present disclosure, there is provided a biometric information measurement device including: the pulse wave detector; and a biometric information calculating section which calculates biometric information based on the pulse wave detected by the pulse wave detector.

DETAILED DESCRIPTION OF THE EMBODIMENTS

Hereinafter, embodiments of the present disclosure will be described with reference to the drawings.

Figure 1:
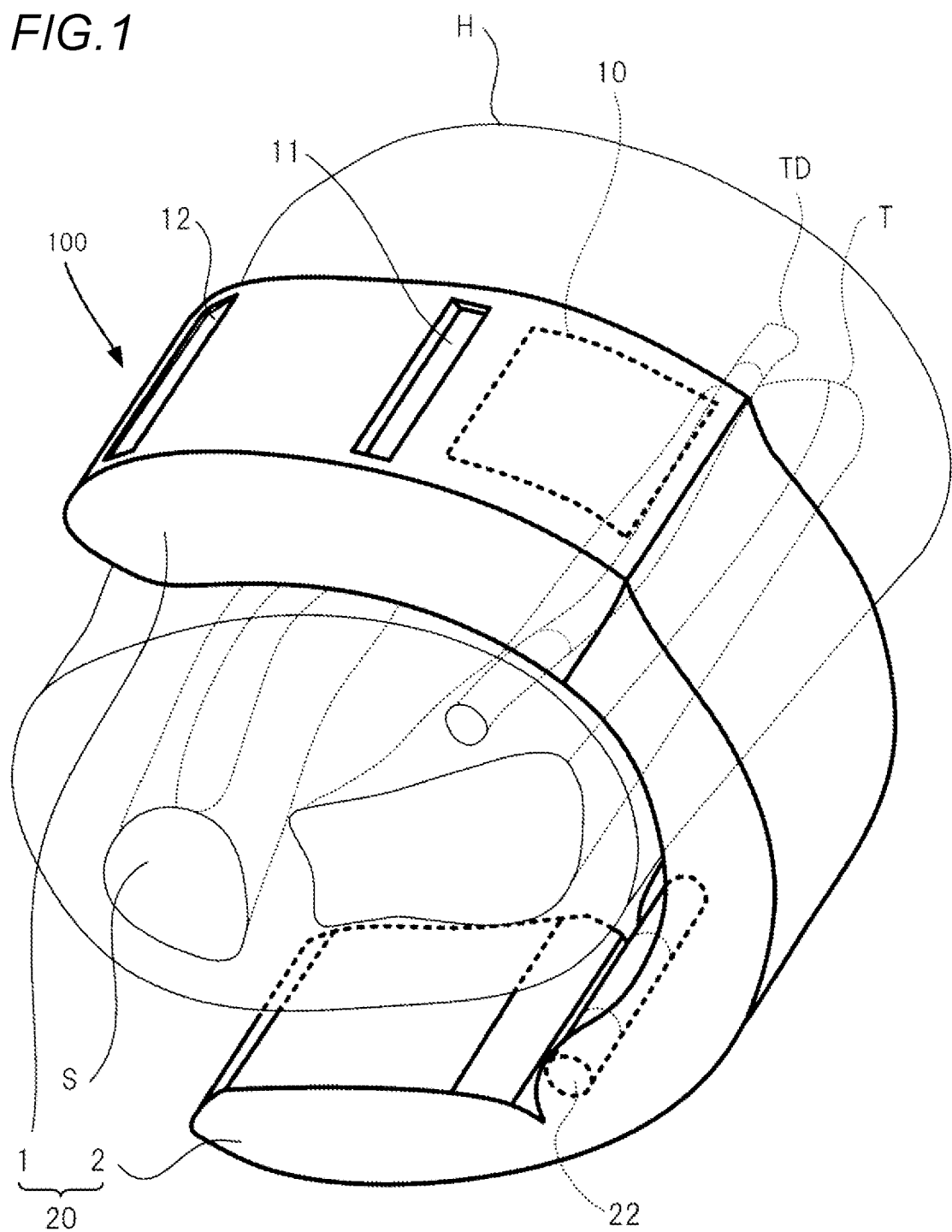
FIG. 1 is a diagram showing the external configuration of a biometric information measurement device 100 for illustrating an embodiment of the present disclosure.

FIG. 1 is a diagram showing the external configuration of a biometric information measurement device 100 for illustrating an embodiment of the present disclosure.

The biometric information measurement device 100 includes a body portion 20, and a strip-shaped band member 3 which is not shown in FIG. 1, and which will be described later. FIG. 1 shows a secured state where the body portion 20 is secured to the wrist H with the band member 3.

FIG. 1 shows the left wrist H of the user of the biometric information measurement device 100. The near side of the figure coincides with the direction in which the hand of the user exists. The upper side of the figure is in the direction along which the palm of the hand is oriented. In the wrist H, the radius T, the ulna S, and the radial artery TD are shown.

The biometric information measurement device 100 has a pulse wave detecting section 10 which detects a pulse wave (a pressure pulse wave or a volume pulse wave) from the radial artery TD that extends along the radius T in the wrist H of the user, and measures biometric information such as the hear rate, the pulse rate, or the blood pressure value based on the pulse wave detected by the pulse wave detecting section 10.

The pulse wave detecting section 10 may have a known configuration. For example, the pulse wave detecting section 10 has a pressure sensor, and a mechanism which presses it against the skin, and detects a pressure pulse wave by using the pressure sensor. Alternatively, the pulse wave detecting section 10 has a photoelectric sensor, and detects a volume pulse wave from a signal detected by the photoelectric sensor. The pressure sensor or the photoelectric sensor constitutes the pulse wave detection sensor.

The body portion 20 of the biometric information measurement device 100 includes the pulse wave detecting section 10, and a biometric information calculating section that is not shown, and that calculates biometric information such as the heart rate, the pulse rate, or the blood pressure value based on the pulse wave detected by the pulse wave detecting section 10.

The biometric information calculating section may be disposed in an apparatus other than the biometric information measurement device 100. Namely, the body portion 20 of the biometric information measurement device 100 is requested to have at least the pulse wave detecting section 10. The biometric information measurement device 100 functions as the pulse wave detector.

The body portion 20 is configured so as to be woundable in the circumferential direction of the wrist H, and to be placed in a position where the process of the ulna S in the wrist H is exposed in the state where the body portion is secured to the wrist H with the band member 3. In other words, the body portion 20 is configured so that the portion between the both ends in the circumferential direction of the wrist H does not cover the ulna S in the state where the body portion is secured to the wrist H with the band member 3.

The body portion 20 is configured by a housing 1 which accommodates the pulse wave detecting section 10, and a housing 2 which is coupled with the housing 1. The housing 2 is coupled with the housing 1 by securing such as adhesion or welding, or detachably coupled with the housing 1 by coupling pins.

The housing 1 is configured mainly by a first rigid member having a high rigidity in order to stabilize the position of the pulse wave detecting section 10 with respect to the radial artery TD in the secured state, and to protect the pulse wave detecting section 10 including precision elements. As the first rigid member, for example, a resin or a metal is used.

A part or the whole of the housing 2 is configured by a second rigid member having a rigidity which is lower than the first rigidity. For example, the housing 2 is configured by the second rigid member in a range extending from the outer circumferential surface (the surface opposite to the surface which is opposed to the wrist H) to a predetermined thickness, and by the first rigid member in the other part.

The member which is lower in rigidity than the housing 1 is used in the outer circumferential surface of the housing 2 as described above, thereby facilitating the housing 2 to be deformed in accordance with the shape of the wrist H. As the second rigid member, for example, an elastic member, a shape-memory alloy, or the like is used.

Although, in FIG. 1, the body portion 20 including the pulse wave detecting section 10 is split into the housing 1 and the housing 2, the body portion may be configured by a completely single member.

A band fastener 22 for securing the band member 3 is disposed on the inner circumferential surface (the surface which is opposed to the wrist H) of the housing 2. In the example of FIG. 1, the band fastener 22 is configured by a columnar metal fitting.

In the outer circumferential surface (the surface opposite to the surface opposed to the wrist H) of the housing 1, hole portions 11, 12 for engaging the band member 3 with the housing 1 are disposed in juxtaposition with each other in the circumferential direction of the wrist H.

Figure 2:
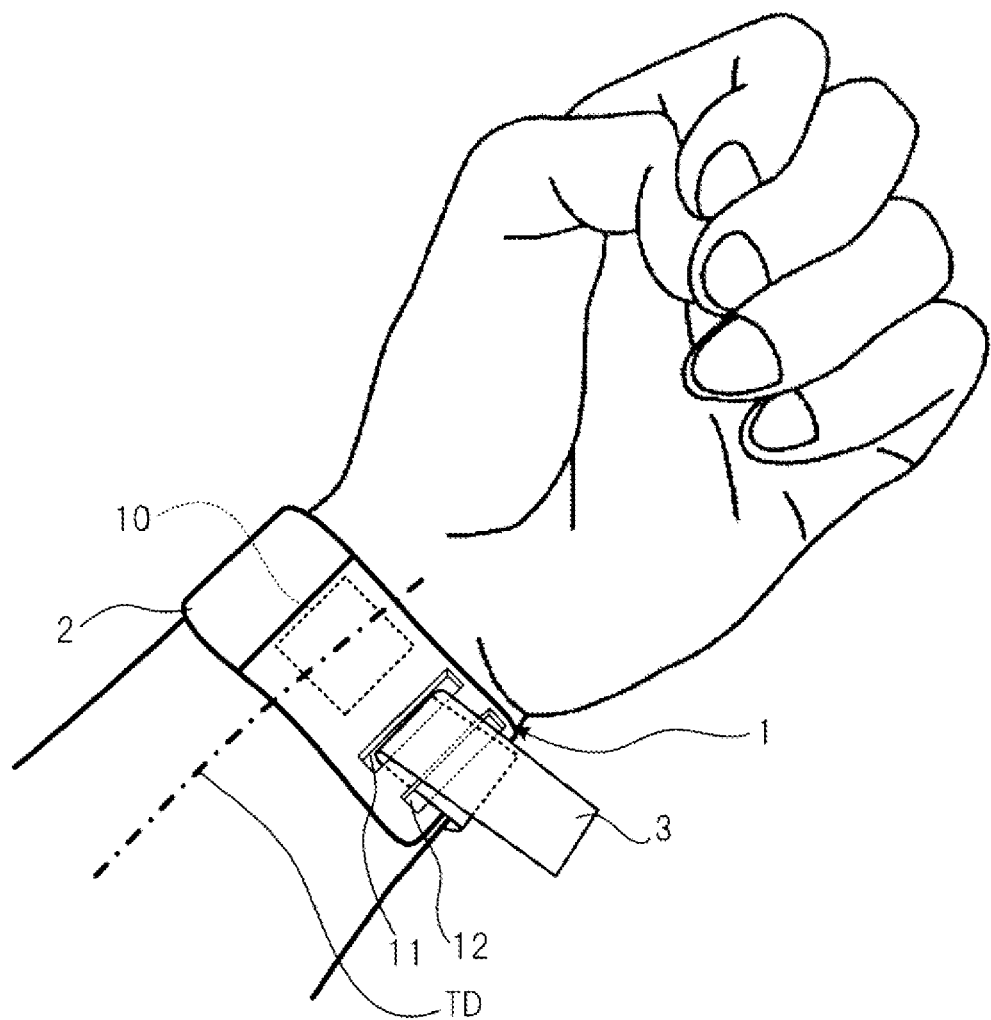
FIG. 2 is a view illustrating a method of securing a body portion 20 to the wrist with a band member 3 of the biometric information measurement device 100.
Figure 3:
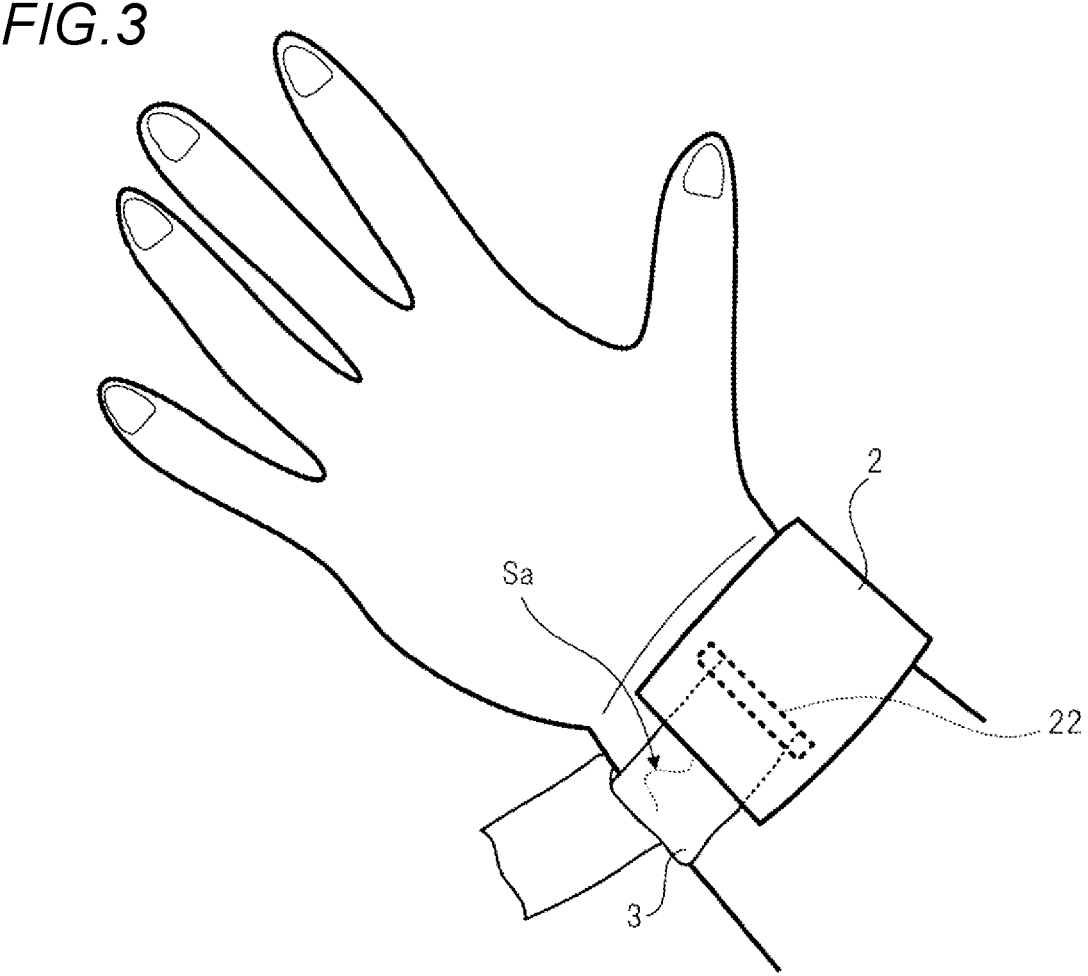
FIG. 3 is a view illustrating the method of securing the body portion 20 to the wrist with the band member 3 of the biometric information measurement device 100.

FIGS. 2 and 3 are views illustrating a method of securing the body portion 20 to the wrist with the band member 3 of the biometric information measurement device 100.

In a state where the body portion 20 is temporarily placed on the wrist, as shown in FIG. 3, the user of the biometric information measurement device 100 moves the tip end of the band member 3 from the back side of the hand toward the hand palm side, inserts the tip end into the hole portion 12, and then pulls out the tip end of the band member 3 from the hole portion 11. The resulting state is the state of FIGS. 2 and 3.

When, in the state of FIGS. 2 and 3, the tip end of the band member 3 is strongly pulled, it is possible to obtain a state where the body portion 20 is secured to the wrist H. In the state, the band member 3 has a part which is in contact with the process Sa of the ulna S that is in the wrist of the user (see FIG. 3).

Figure 4:
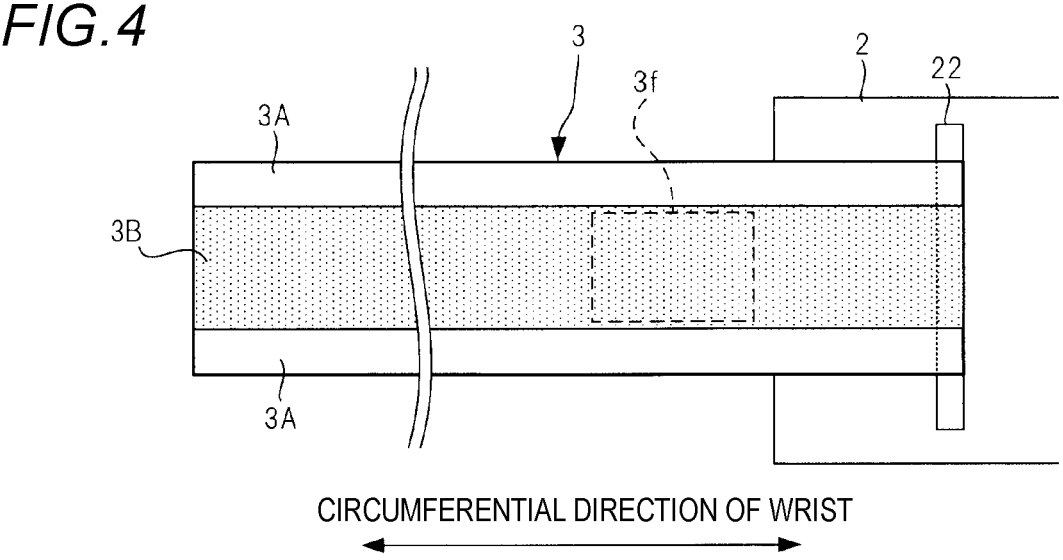
FIG. 4 is a plan view of the band member 3 which is secured to a band fastener 22, as seen from a side of a contact surface with respect to the wrist.
Figure 5:
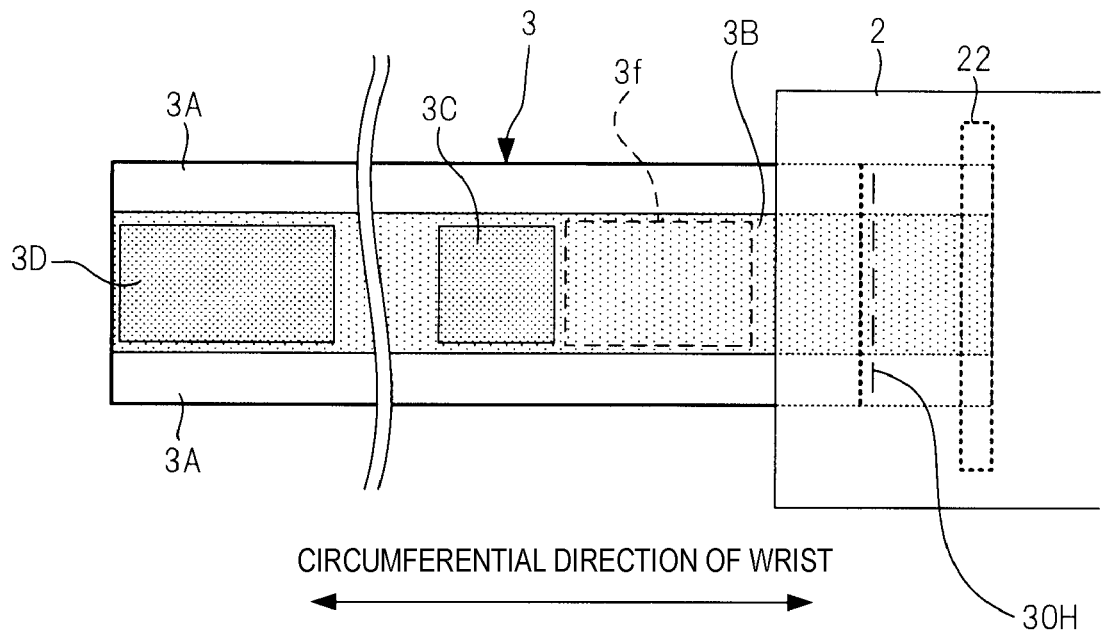
FIG. 5 is a plan view of the band member 3 which is secured to the band fastener 22, as seen from the side of a surface opposite to the contact surface with respect to the wrist.

FIG. 4 is a plan view of the band member 3 which is secured to the band fastener 22, as seen from the side of the contact surface with respect to the wrist. FIG. 5 is a plan view of the band member 3 which is secured to the band fastener 22, as seen from the side of the surface opposite to the contact surface with respect to the wrist. FIGS. 4 and 5 are plan views of a state where the band member 3 is developed in one direction (the direction in which the band member is wound around the wrist), as seen in directions which are perpendicular respectively to the one direction and the short side direction of the band member 3.

The band member 3 is a strip-shaped member which extends in the longitudinal direction (synonymous with the circumferential direction of the wrist H) of the body portion 20. The band member 3 is configured by a member which is lower in rigidity than the body portion 20, such as cloth, leather, or rubber.

In the example shown in FIGS. 4 and 5, the band member 3 has two first regions 3A which are juxtaposed with a gap in the short side direction, and a second region 3B which is disposed between the two first regions 3A, and which is higher in stretchability than the first regions 3A. Each of the first regions 3A and the second region 3B has a rectangular shape which extends from one end in the longitudinal direction of the band member 3 to the other end.

The stretchability of a member is a characteristic indicating the degree in which, when a force is applied to the member, the member extends in the application direction of the force. When a predetermined force is applied to an arbitrary region, the larger the elongation amount of the arbitrary region in the application direction of the force, the higher the stretchability of the arbitrary region.

Figure 9:
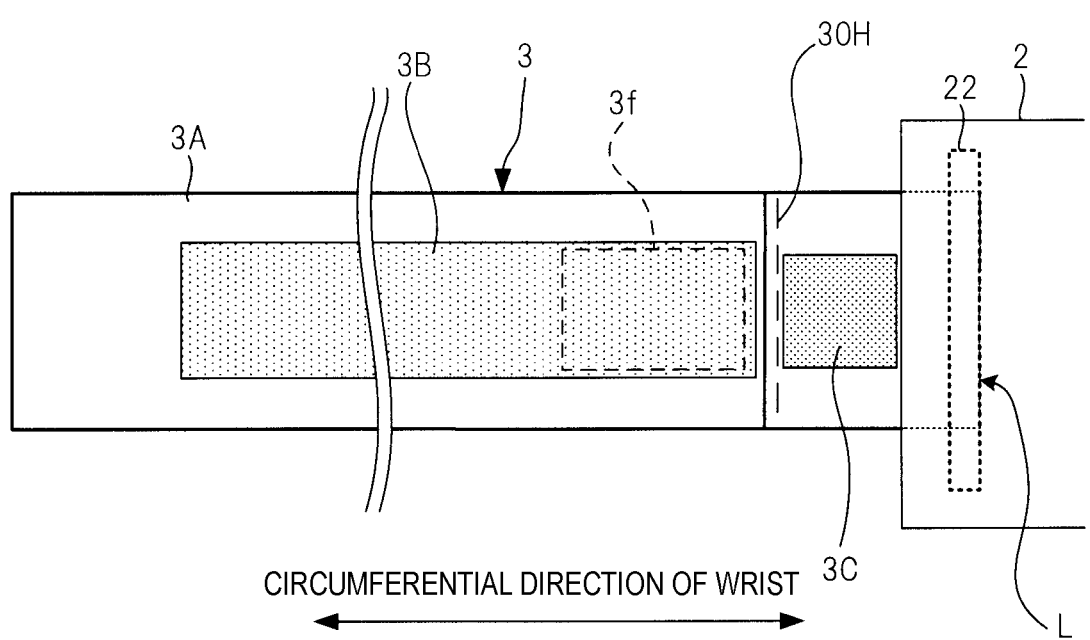
FIG. 9 is a view showing a fourth modification of the biometric information measurement device 100.
Figure 10:
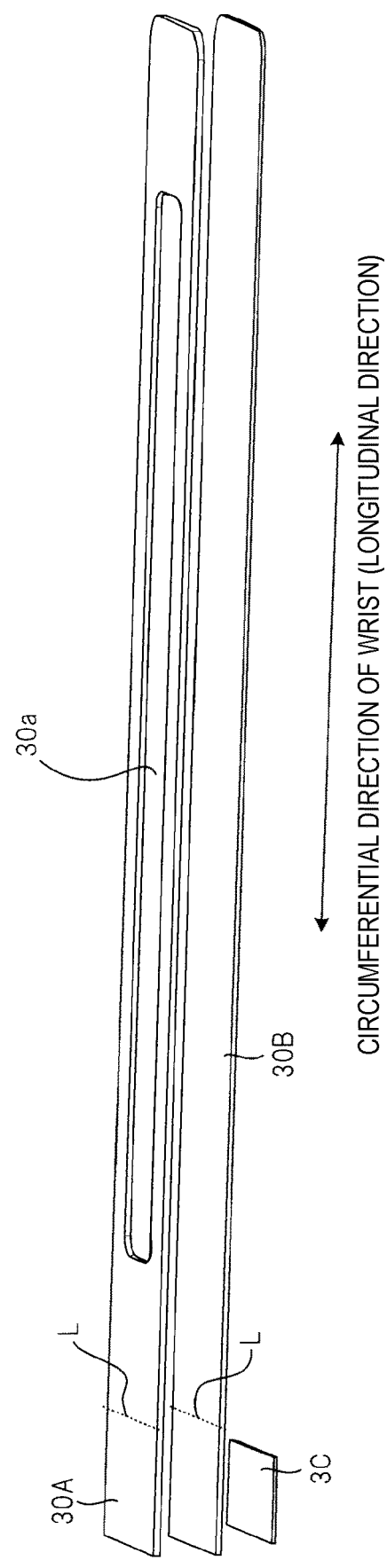
FIG. 10 is an exploded perspective view of the band member 3 shown in FIG. 9.
Figure 11:
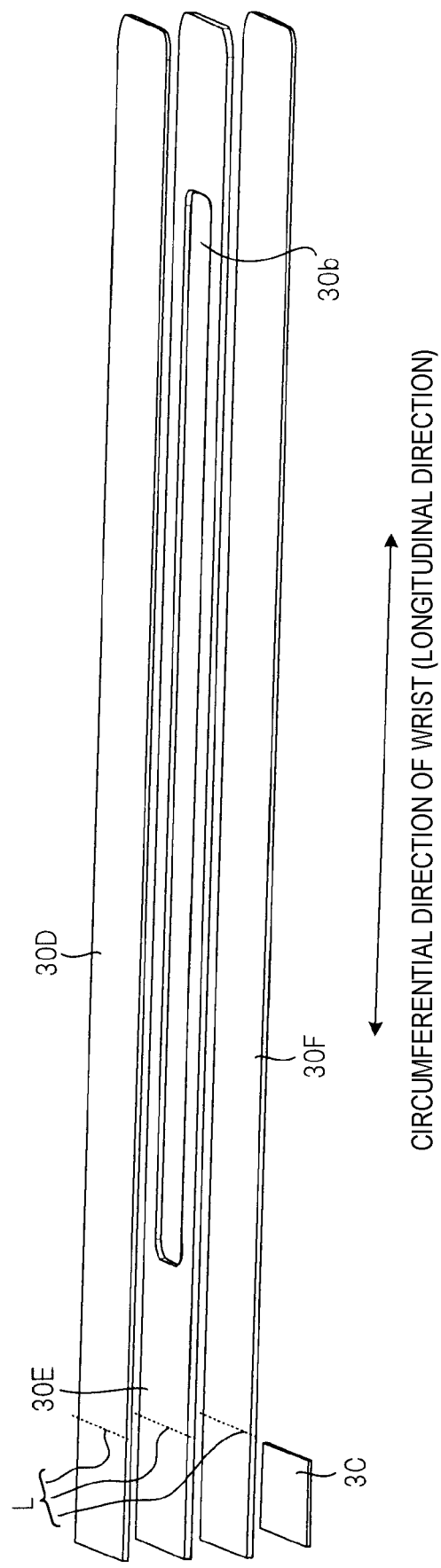
FIG. 11 is an exploded perspective view showing a modification of the band member 3 of the biometric information measurement device 100 shown in FIG. 9.

Examples of the configuration where the stretchability of the first regions 3A and that of the second region 3B are different from each other are: a configuration where the first regions 3A and the second region 3B are formed by materials having different stretchabilities; that where the first regions 3A and the second region 3B are formed by the same material, and the second region 3B is thinner than the first regions 3A; that where the first regions 3A and the second region 3B are formed by different materials, and the second region 3B is thinner than the first regions 3A; that where the first regions 3A and the second region 3B are formed by knitting with threads having the same quality, and their knitting processes are performed in different manners; and that where the first regions 3A and the second region 3B are formed materials having different stretchabilities, and the second region 3B is thinner than the first regions 3A (see FIGS. 9 to 11 which will be described later).

The basal end portion (the one end portion) in the longitudinal of the band member 3 is secured to the housing 2. Specifically, portions of the same surface of the band member 3 are bonded or sewn to each other in a state where the basal end side in the longitudinal direction is wound back from the band fastener 22, whereby the band member 3 is secured to the band fastener 22. The reference numeral 30H in FIG. 5 denotes the portion where the basal end side of the band member 3 is wound back and sewn or bonded to another portion. A tip end portion (other end portion) in the longitudinal direction of the band member 3 is in a free state where the portion is not supported by any member.

The method of securing the basal end portion of the band member 3 to the housing 2 is not limited the above-described method. For example, a configuration in which the basal end portion of the band member 3 is secured to the housing 2 by using screws or the like may be employed. Alternatively, a configuration in which the basal end portion of the band member 3 is secured to the band fastener 22 by using a hook and loop fastener may be employed.

The second region 3B of the band member 3 is in contact with the process Sa of the ulna in the wrist H in the secured state where the body portion 20 is secured to the wrist H with the band member 3. The diameter of the wrist H and the position of the process Sa of the ulna are different among individuals. When data of hand shapes of many persons are used, however, it is possible to design the band member 3 in which the second region 3B is in contact with the process Sa of the ulna in the secured state. The range 3$f$ which is indicated by the broken line in FIGS. 4 and 5 indicates a range which is obtained by using data of hand shapes of many persons, and in which the band member 3 can be contacted with the process Sa of the ulna.

As shown in FIG. 5, a hook portion 3C in which fabrics are raised in hook-like shapes to constitute a hook and loop fastener, and a loop portion 3D in which fabrics are densely raised in loop-like shapes to constitute the hook and loop fastener are formed on the surface opposite to the contact surface of the band member 3 which is to be in contact with the wrist H in the secured state. The hook portion 3C constitutes the coupled portion, and the loop portion 3D constitutes the coupling portion.

The hook and loop fastener which is configured by the hook portion 3C and the loop portion 3D constitutes means for detachably coupling a part of the band member 3 with another part of the band member 3.

The loop portion 3D is disposed in the tip end portion of the band member 3. The hook portion 3C is disposed in a portion of the surface opposite to the contact surface of the band member 3 which is to be in contact with the wrist H, excluding the range 3$f$ and the loop portion 3D.

In the state shown in FIGS. 2 and 3, the user pulls the tip end portion of the band member 3, and winds the band member 3 around the wrist H. Then, the user applies the loop portion 3D disposed on the band member 3, to the hook portion 3C disposed on the band member 3. As a result, the securing of the body portion 20 to the wrist H with the band member 3 is completed.

As described above, the biometric information measurement device 100 has the configuration in which the band member 3 for securing the body portion 20 to the wrist H includes the first regions 3A and the second region 3B. In the secured state, the second region 3B is in contact with the process Sa of the ulna. The second region 3B is higher in stretchability than the first regions 3A. In the state where the band member 3 is wound around the wrist H as shown in FIGS. 2 and 3, therefore, the force which is applied from the process Sa of the ulna to the second region 3B is reduced by extension of the second region 3B. As a result, a pressure which is applied from the band member 3 to the process Sa of the ulna is reduced.

According to the biometric information measurement device 100, as described above, securing of the body portion 20 is enabled without imposing a burden on the wrist. Therefore, the user strongly winds the band member 3 to cause the body portion 20 to be secured to the wrist, and the close contactness between the body portion 20 and the wrist H can be improved. As a result, the pulse wave detecting section 10 can be prevented from being displaced from a desired position, and a pulse wave can be accurately detected.

In the biometric information measurement device 100, moreover, the hook portion 3C and loop portion 3D which constitute the hook and loop fastener are disposed in portions other than the range 3f in the surface opposite to the contact surface with respect to the wrist in the band member 3. Therefore, it is possible to prevent the stretchability of the second region 3B in the range 3f from being lowered, and the pressure which is exerted from the band member 3 to the process Sa of the ulna can be effectively lowered.

Moreover, the hook and loop fastener does not exist in the portion which is to overlap with the range 3f. When the hook portion 3C and the loop portion 3D are applied together, therefore, it is possible to prevent the band member 3 from being doubly closely placed above the process Sa of the ulna. Consequently, the pressure which is applied to the process Sa of the ulna in the secured state can be prevented from being increased, and the attachability of the biometric information measurement device 100 can be improved.

The hook portion 3C may overlap with the range 3f. In this case, the stretchability of the second region 3B in a state where it includes the hook portion 3C is requested to be higher than that of the first regions 3A.

The band member 3 of the biometric information measurement device 100 has the first regions 3A. The first regions 3A are lower in stretchability than the second region 3B. When the band member 3 is wound around the wrist, therefore, it is possible to prevent the whole band member 3 from excessively extending in the circumferential direction of the wrist, and the attachability of the biometric information measurement device 100 can be improved. In the secured state, moreover, the whole band member 3 is prevented from extending in the circumferential direction of the wrist. Therefore, the positional displacement of the pulse wave detecting section 10 can be prevented from occurring, and a pulse wave can be accurately detected.

In the second region 3B of the band member 3, the stretchability in the short side direction (the direction perpendicular to the longitudinal direction) of the band member 3 is preferably higher than that of the band member 3 in the longitudinal direction of the band member 3.

For example, a configuration is preferable where the stretchability of the first regions 3A in the longitudinal direction of the band member 3 is identical with that of the second region 3B in the longitudinal direction of the band member 3 (the term "identical" may involve some tolerances), and the stretchability of the second region 3B in the short side direction of the band member 3 is higher than that of the first regions 3A in the short side direction of the band member 3.

According to the configuration, the force which causes the band member 3 in the secured state to extend in the longitudinal direction is suppressed, and therefore the positional displacement of the body portion 20 due to a motion of the wrist or the like can be prevented from occurring. In the second region 3B, moreover, the band member 3 easily extends in the short side direction of the band member 3. Therefore, it is possible to prevent the pressure which is applied to the process Sa of the ulna in the secured state, from being increased, and the attachability of the biometric information measurement device 100 can be improved.

Next, modifications of the biometric information measurement device 100 will be described.

First Modification

Figure 6:
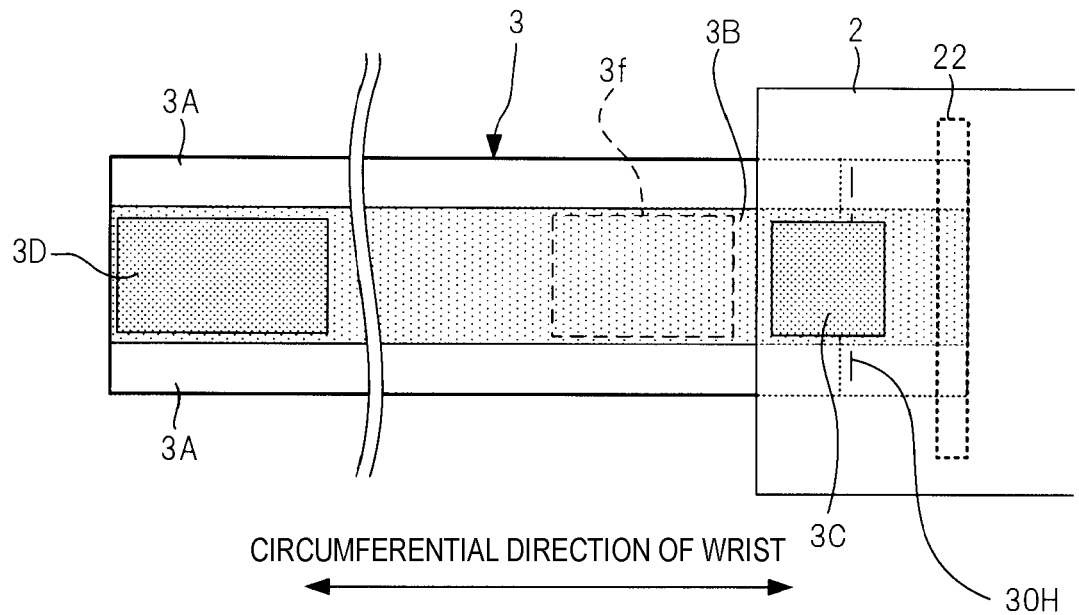
FIG. 6 is a view showing a first modification of the biometric information measurement device 100.

FIG. 6 is a view showing a first modification of the biometric information measurement device 100, and corresponding to FIG. 5. The biometric information measurement device 100 shown in FIG. 6 is configured in the same manner as FIG. 5 except that the position of the hook portion 3C is changed to a position on the outer circumferential surface of the housing 2.

According to the configuration, when the hook portion 3C and the loop portion 3D are applied together, it is possible to prevent the band member 3 from being doubly closely placed above the process Sa of the ulna, and the attachability of the biometric information measurement device 100 can be improved.

Although, in FIGS. 5 and 6, a hook and loop fastener is used as means for maintaining the state where the body portion 20 is secured to the wrist with the band member 3, the means is not limited to a hook and loop fastener.

For example, a clasp member which is used in a known watchband may be employed. Even in the case where a clasp member is employed as means for detachably coupling a part of the band member 3 with another part of the band member 3, or means for detachably coupling a part of the band member 3 with the housing 2, when the clasp member is disposed in a position excluding the range 3f, the attachability of the biometric information measurement device 100 can be improved.

Second Modification

Figure 7:
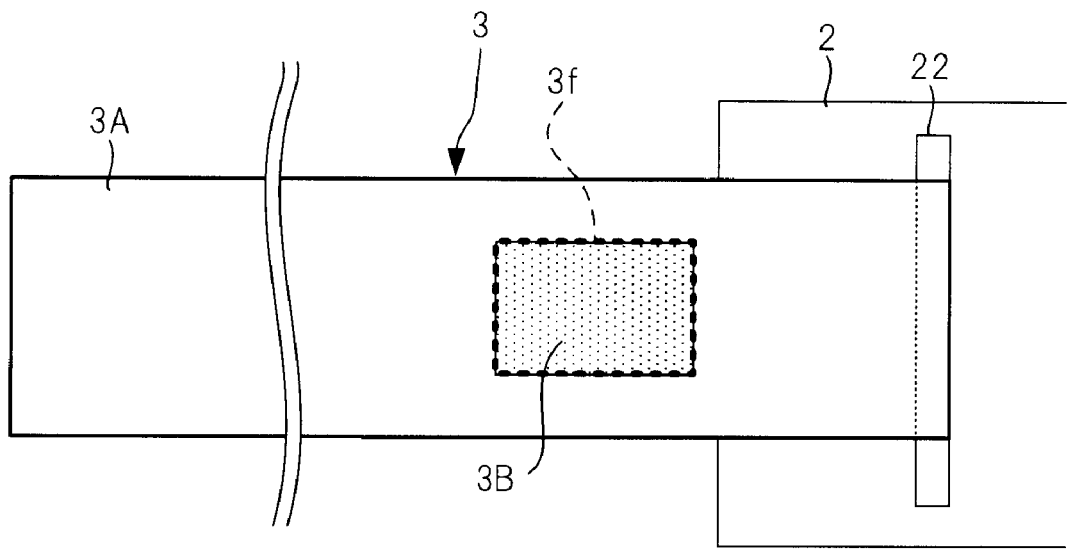
FIG. 7 is a view showing a second modification of the biometric information measurement device 100.

FIG. 7 is a view showing a second modification of the biometric information measurement device 100, and corresponding to FIG. 4. The biometric information measurement device 100 shown in FIG. 7 is configured in the same manner as FIG. 4 except that the first region 3A and second region 3B of the band member 3 have different shapes.

In the band member 3 shown in FIG. 7, the above-described range 3f is configured by the second region 3B, and the region other than the second region 3B is configured by the first region 3A.

According to the configuration, the majority of the band member 3 is configured by the first region 3A, and therefore the force which causes the band member 3 in the secured state to extend in the longitudinal direction is suppressed. Consequently, the positional displacement of the body portion 20 due to a motion of the wrist or the like can be prevented from occurring. Since the second region 3B has high stretchability, it is possible to prevent the pressure which is applied to the process Sa of the ulna, from being increased, and the attachability of the biometric information measurement device 100 can be improved.

Third Modification

Figure 8:
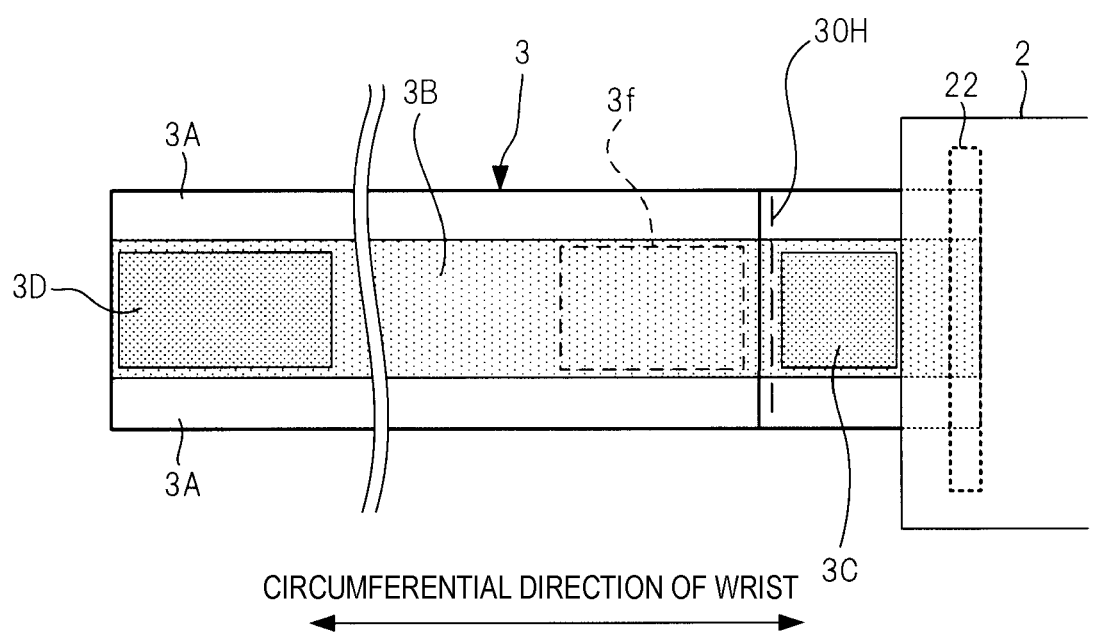
FIG. 8 is a view showing a third modification of the biometric information measurement device 100.

FIG. 8 is a view showing a third modification of the biometric information measurement device 100, and corresponding to FIG. 5. The biometric information measurement device 100 shown in FIG. 8 is configured in the same manner as FIG. 5 except that the length of the housing 2 in the circumferential direction of the wrist is shortened, and the hook portion 3C is disposed in a different position.

In the biometric information measurement device 100 shown in FIG. 8, the hook portion 3C of the band member 3 is disposed between the range 3f and an end portion of the housing 2.

In the configuration shown in FIG. 8, in the state where the hook portion 3C and the loop portion 3D are applied together, two members or the two portions of the second region 3B overlap with each other above the process Sa of the ulna. Even in the configuration where the band member 3 doubly overlaps with the process Sa of the ulna as described above, the stretchability of the second region 3B is high, and therefore the pressure which is applied to the process Sa of the ulna can be lowered.

In the case where the stretchability of the second region 3B is relatively high because the second region 3B is smaller in thickness than the first regions 3A, even when the second region 3B doubly overlaps with the process Sa of the ulna, particularly, the thickness can be suppressed, and therefore the influence on the attachability of the device is weak.

Fourth Modification

FIG. 9 is a view showing a fourth modification of the biometric information measurement device 100, and corresponding to FIG. 5. The band member 3 of the biometric information measurement device 100 shown in FIG. 9 is configured in the same manner as FIG. 8 except that the second region 3B is surrounded by the first region 3A, the loop portion 3D is deleted, and a loop portion is formed on the surface opposite to the contact surface with respect to the wrist in the first region 3A.

FIG. 10 is an exploded perspective view of the band member 3 shown in FIG. 9.

As shown in FIG. 10, the band member 3 of the biometric information measurement device 100 shown in FIG. 9 includes a first member 30A, a second member 30B which is secured to the rear surface of the first member 30A, and the hook portion 3C which is secured to the rear surface of the second member 30B.

The band member 3 is folded back in a folding line L so that the hook portion 3C is located above the front surface of the first member 30A. In the band member 3, the rear surface of the second member 30B other than the folded back portion constitutes a contact surface which is to be in contact with the wrist. Moreover, the surface on which the hook portion 3C that is to be folded back and secured to the front surface of the first member 30A is formed, and the front surface of the first member 30A other than the surface constitute the surface opposite to the contact surface.

The first member 30A is a strip-shaped member which extends along the circumferential direction of the wrist, and has an opening 30a. The plan shape of the opening 30a is identical with that of the second region 3B shown in FIG. 9, and, in the secured state, the opening 30a covers the above-described range 3f. A loop portion which cooperates with the hook portion 3C to constitute a hook and loop fastener is formed on the front surface of the first member 30A.

The second member 30B is a strip-shaped member which extends along the circumferential direction of the wrist, and made of a material which is higher in stretchability than the first member 30A.

The hook portion 3C is secured to the rear surface of a tip end portion (the portion which is on the tip end side of the folding line L) of the second member 30B.

In the band member 3 shown in FIG. 10, the overlapping portions of the first member 30A and the second member 30B constitute the first region 3A. Moreover, the overlapping portion of the opening 30a of the first member 30A, and the second member 30B constitutes the second region 3B. According to the configuration of FIG. 10, the band member 3 is configured into the two-layer structure, and therefore the pressure which is applied from the ulna is caused to escape, and the attachability can be improved while sufficiently ensuring the winding strength of the band member 3.

Fifth Modification

FIG. 11 is an exploded perspective view showing a modification of the band member 3 of the biometric information measurement device 100 shown in FIG. 9.

The band member 3 shown in FIG. 11 includes a third member 30D, a fourth member 30E which is secured to the rear surface of the third member 30D, a fifth member 30F which is secured to the rear surface of the fourth member 30E, and the hook portion 3C which is secured to the rear surface of the fifth member 30F.

The band member 3 is folded back in a folding line L so that the hook portion 3C is located above the front surface of the third member 30D. In the band member 3, the rear surface of the fifth member 30F other than the folded back portion constitutes a contact surface which is to be in contact with the wrist. Moreover, the surface on which the hook portion 3C that is to be folded back and secured to the front surface of the third member 30D is formed, and the front surface of the third member 30D other than the surface constitute the surface opposite to the contact surface.

The third member 30D is a strip-shaped member which extends along the circumferential direction of the wrist. A loop portion which cooperates with the hook portion 3C to constitute a hook and loop fastener is formed on the front surface of third member 30D.

The fourth member 30E is a strip-shaped member which extends along the circumferential direction of the wrist, and has an opening 30b. The plan shape of the opening 30b is identical with that of the second region 3B shown in FIG. 9, and, in the secured state, the opening 30b covers the above-described range 3f.

The fifth member 30F is a strip-shaped member which extends along the circumferential direction of the wrist, and made of a material which is higher in stretchability than the third member 30D and the fourth member 30E.

The hook portion 3C is secured to the rear surface of a tip end portion (the portion which is on the tip end side of the folding line L) of the fifth member 30F.

In the band member 3 shown in FIG. 11, the overlapping portions of the third member 30D, the fourth member 30E, and the fifth member 30F constitute the first region 3A. Moreover, the overlapping portion of the third member 30D, the opening 30b of the fourth member 30E, and the fifth member 30F constitutes the second region 3B. According to the configuration of FIG. 11, the band member 3 is configured into the three-layer structure, and therefore the pressure which is applied from the ulna is caused to escape, and the attachability can be improved while sufficiently ensuring the winding strength of the band member 3.

In the biometric information measurement device 100 which has been described above, the body portion 20 is placed in a position where the process Sa of the ulna is exposed in the secured state. The present disclosure can be applied also to a biometric information measurement device in which a body portion is placed in a position where the process of the radius is exposed in the secured state.

Figure 12:
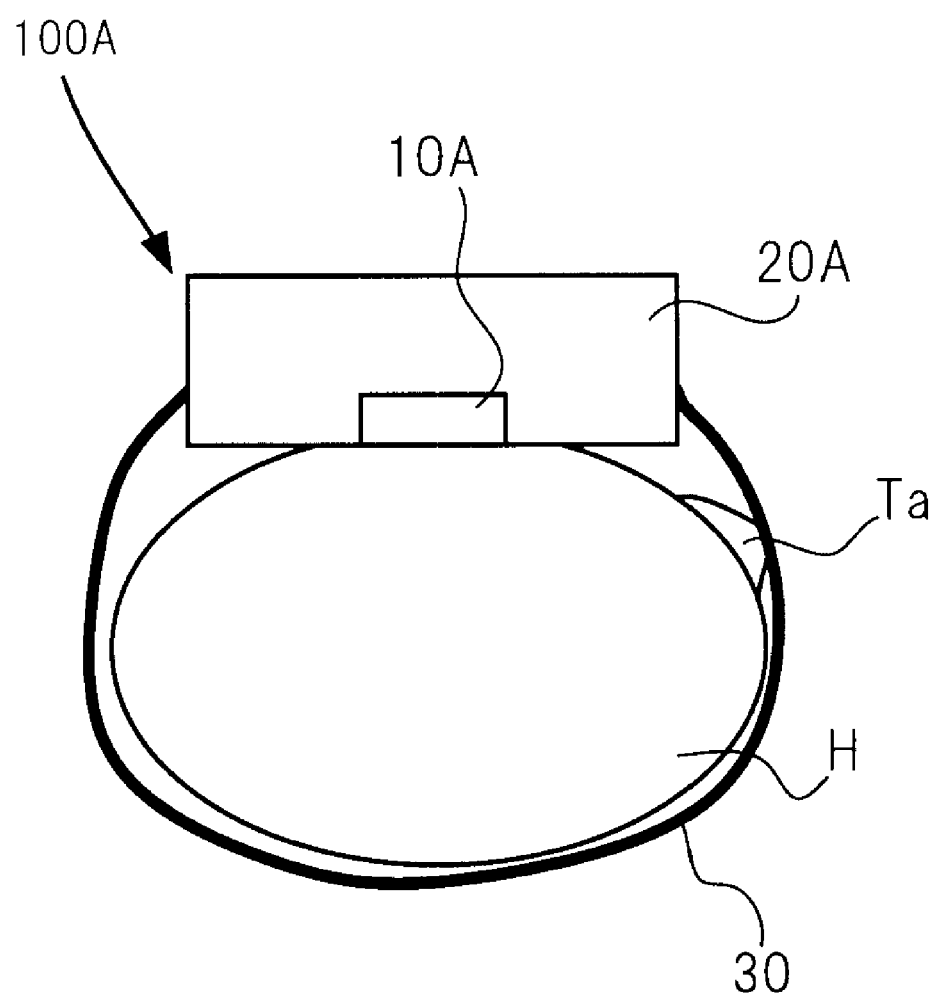
FIG. 12 is a diagram showing the configuration of a biometric information measurement device 100A for illustrating an embodiment of the present disclosure.

For example, the present disclosure can be applied also to a biometric information measurement device 100A in which, as shown in FIG. 12, a body portion 20A including a pulse wave detecting section 10A is secured to the hand back side of the wrist H with a strip-shaped band member 30.

In the biometric information measurement device 100A, the body portion 20A is placed in a position where the process Ta of the radius is exposed in a state where the body portion 20A is secured to the wrist H with the band member 30. In the state where the body portion 20A is secured to the wrist H with the band member 30, a part of the band member 30 is in contact with the process Ta of the radius.

When, in the band member 30, the range where the member can contacted with the process Ta of the radius is set as the above-described second range 3B, and the region other than the second range 3B is set as the above-described first region 3A, therefore, the pressure which is applied from the band member 30 to the process Ta of the radius is lowered, and the attachability of the biometric information measurement device can be improved.

The presently disclosed embodiment should be considered in all respects to be illustrative and not restrictive. The scope of the invention is indicated by the appended claims rather than the foregoing description, and all changes which come within the meaning and range of equivalents thereof are intended to be embraced therein.

As described above, the following matters are disclosed in the specification.

Disclosed is a pulse wave detector comprising: a body portion including a pulse wave detection sensor which detects a pulse wave from an artery in a wrist of a user; and a strip-shaped band member for securing the body portion to the wrist, wherein in a secured state where the body portion is secured to the wrist with the band member, the body portion is placed in a position where a process of an ulna in the wrist or a process of a radius in the wrist is exposed, wherein the band member includes a first region, and a second region which is higher in stretchability than the first region, and wherein in the secured state, the second region is at least in contact with the process of the ulna in the wrist or the process of the radius in the wrist.

According to the disclosed pulse wave detector, a stretchability of the second region in a longitudinal direction of the band member is lower than a stretchability of the second region in a direction perpendicular to the longitudinal direction.

According to the disclosed pulse wave detector, the stretchability of the second region in the longitudinal direction of the band member is identical with a stretchability of the first region in the longitudinal direction.

According to the disclosed pulse wave detector, the band member has a hook and loop fastener for detachably coupling together a part of the band member and another part, on a surface opposite to a surface which is in contact with the wrist, and at least one of a coupled portion of the hook and loop fastener, and a coupling portion which is coupled with the coupled portion is disposed on a surface of the opposite surface other than a region where, in the secured state, the portion overlaps with the process of the ulna in the wrist or the process of the radius in the wrist.

According to the disclosed pulse wave detector, the band member has a first portion which, in the secured state, is in contact with the process of the ulna in the wrist or the process of the radius in the wrist, and a second portion which overlaps with the first portion, and the first portion and the second portion are the second region.

Disclosed is a biometric information measurement device including: the pulse wave detector; and a biometric information calculating section which calculates biometric information based on the pulse wave detected by the pulse wave detector.

According to the present disclosure, it is possible to provide a pulse wave detector in which the feeling and easiness of attachment to the wrist are improved, and a pulse wave can be accurately detected, and also a biometric information measurement device including the detector.

The present disclosure is very convenient and effective particularly in application to a blood pressure monitor or the like.

Although the present disclosure has been described with reference to the specific embodiments, the invention is not limited to the embodiments, and various changes can be made without departing from the technical spirit of the invention.

What is claimed is:

1. A pulse wave detector comprising:
a body portion including a pulse wave detection sensor that detects a pulse wave from an artery in a wrist of a user; and
a strip-shaped band member configured to secure the body portion to the wrist, the band member including two first regions and a second region, which is higher in stretchability than a stretchability of each of the two first regions in a short side direction perpendicular to a longitudinal direction of the band member, the two first regions being juxtaposed with a gap in the short side direction of the band member, the second region being disposed between the two first regions in the short side direction of the band member, and the band member including a hook and loop fastener configured to detachably couple together a first part of the band member and a second part of the band member, on a surface opposite to a surface that is in contact with the wrist, wherein:
in a secured state where the body portion is secured to the wrist with the band member, the body portion is placed in a position such that a process of an ulna in the wrist or a process of a radius in the wrist is exposed,
in the secured state, the second region is at least in contact with the process of the ulna in the wrist or the process of the radius in the wrist,
at least one of a coupled portion of the hook and loop fastener, and a coupling portion at that is coupled with the coupled portion is disposed on a region of the opposite surface other than a region which, in the secured state, overlaps with the process of the ulna in the wrist or the process of the radius in the wrist, and
each of the two first regions and the second region extends from a first free end of the band member to a second opposite free end of the band member in the longitudinal direction of the band member.

2. A biometric information measurement device including:
the pulse wave detector according to claim 1; and
a biometric information calculating circuit that calculates biometric information based on the pulse wave detected by the pulse wave detector.

3. The pulse wave detector according to claim 1, wherein a stretchability of the second region in the longitudinal direction of the band member is lower than a stretchability of the second region in the short side direction.

4. The pulse wave detector according to claim 1, wherein a stretchability of the second region in the longitudinal direction of the band member is identical with a stretchability of each of the two the first regions in the longitudinal direction.

5. The pulse wave detector according to claim 1, wherein the band member has a first portion that, in the secured state, is in contact with the process of the ulna in the wrist or the process of the radius in the wrist, and a second portion that overlaps with the first portion, and the first portion and the second portion are the second region.

6. A biometric information measurement device including:
   the pulse wave detector according to claim 3; and
   a biometric information calculating circuit that calculates biometric information based on the pulse wave detected by the pulse wave detector.

7. A biometric information measurement device including:
   the pulse wave detector according to claim 4; and
   a biometric information calculating circuit that calculates biometric information based on the pulse wave detected by the pulse wave detector.

8. A biometric information measurement device including:
   the pulse wave detector according to claim 5; and
   a biometric information calculating circuit that calculates biometric information based on the pulse wave detected by the pulse wave detector.

* * * * *